United States Patent
Jimenez, Jr. et al.

(10) Patent No.: US 6,780,183 B2
(45) Date of Patent: Aug. 24, 2004

(54) ABLATION CATHETER HAVING SHAPE-CHANGING BALLOON

(75) Inventors: Teodoro S. Jimenez, Jr., Corona, CA (US); Pete B. Klumb, Corona Del Mar, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 133 days.

(21) Appl. No.: 10/244,355

(22) Filed: Sep. 16, 2002

(65) Prior Publication Data

US 2004/0054367 A1 Mar. 18, 2004

(51) Int. Cl.$^7$ .............................................. A61B 18/18
(52) U.S. Cl. .......................... 606/41; 606/28; 606/192; 600/462
(58) Field of Search .............................. 606/27, 28, 41, 606/192, 194; 607/101–105; 604/96.01, 102.02, 103, 103.07; 600/439, 459, 462, 466

(56) References Cited

U.S. PATENT DOCUMENTS

| | | | |
|---|---|---|---|
| 4,564,014 A | | 1/1986 | Fogarty et al. |
| 4,946,440 A | | 8/1990 | Hall |
| 5,041,089 A | * | 8/1991 | Mueller et al. ........ 604/103.09 |
| 5,246,421 A | | 9/1993 | Saab |
| 5,540,679 A | * | 7/1996 | Fram et al. ................... 606/27 |
| 5,575,772 A | * | 11/1996 | Lennox .................... 604/96.01 |
| 5,630,837 A | | 5/1997 | Crowley |
| 5,649,908 A | * | 7/1997 | Itoh ........................ 604/96.01 |
| 5,676,654 A | | 10/1997 | Ellis et al. |
| 5,766,151 A | | 6/1998 | Valley et al. |
| 5,782,760 A | | 7/1998 | Schaer |
| 5,860,974 A | | 1/1999 | Abele |
| 5,899,860 A | | 5/1999 | Pfeiffer et al. |
| 5,961,536 A | * | 10/1999 | Mickley et al. ............. 606/194 |
| 6,004,269 A | | 12/1999 | Crowley et al. |

(List continued on next page.)

FOREIGN PATENT DOCUMENTS

| | | |
|---|---|---|
| EP | 1 042 990 A1 | 10/2000 |
| WO | WO 00/56237 A3 | 9/2000 |

*Primary Examiner*—Michael Peffley
(74) *Attorney, Agent, or Firm*—Christie, Parker & Hale, LLP

(57) ABSTRACT

A circumferential ablation catheter is provided that is particularly useful for ablating a circumferential region of tissue in a tubular region of or near the heart, such as a pulmonary vein. The catheter comprises an elongated tubular catheter body having an outer wall, proximal and distal ends, and a lumen extending therethrough. The catheter also comprises a generally tubular inner support member having proximal and distal ends and a lumen extending therethrough. A proximal portion of the inner support member extends into the lumen of the catheter body, and a distal portion of the inner support member extends outside the catheter body. A circumferential ablation element, such as an ultrasound transducer, is mounted on the distal portion of the inner support member outside the catheter body. A moveable tube extends through the lumen of the inner support member and through the catheter body. The moveable tube is longitudinally moveable relative to the inner support member and catheter body and has a distal end that extends beyond the distal end of the inner support member. An inflatable balloon is provided generally in surrounding relation to the circumferential ablation element. The inflatable balloon has a proximal end attached, directly or indirectly, to the distal end of the catheter body and a distal end attached, directly or indirectly, to a portion of the moveable tube that extends beyond the distal end of the inner support member. Longitudinal movement of the moveable tube relative to the catheter body and inner support member causes movement of the distal end of the balloon relative to the proximal end of the balloon to thereby change the length and shape of the expanded balloon.

39 Claims, 7 Drawing Sheets

U.S. PATENT DOCUMENTS

| | | |
|---|---|---|
| 6,024,740 A | 2/2000 | Lesh et al. |
| 6,039,721 A | 3/2000 | Johnson et al. |
| 6,117,101 A | 9/2000 | Diederich et al. |
| 6,231,572 B1 | 5/2001 | Hart et al. |
| 6,251,093 B1 | 6/2001 | Valley et al. |
| 6,383,151 B1 | 5/2002 | Diederich et al. |
| 6,427,089 B1 | 7/2002 | Knowlton |
| 2001/0034518 A1 | 10/2001 | Edwards et al. |
| 2002/0065512 A1 | 5/2002 | Fjield et al. |

\* cited by examiner

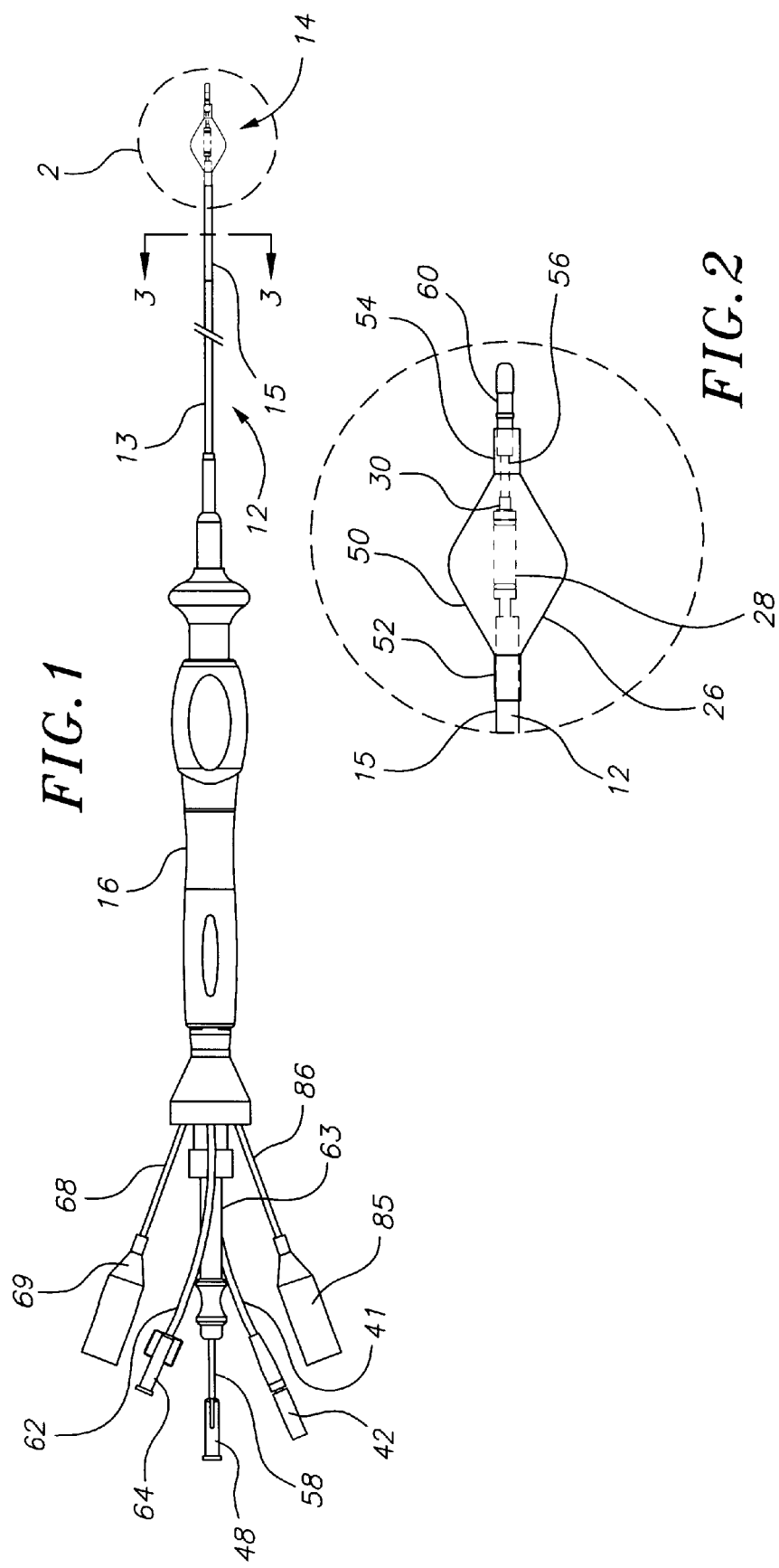

ABLATION CATHETER HAVING SHAPE-CHANGING BALLOON

FIELD OF THE INVENTION

The present invention relates to an improved ablation catheter that is particularly useful for ablating tissue in a tubular region of or near the heart.

BACKGROUND OF THE INVENTION

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, although such pharmacological solutions are not generally believed to be entirely effective in many cases, and may in some cases result in proarrhythmia and long term inefficacy. Several surgical approaches have also been developed with the intention of treating atrial fibrillation. One particular example is known as the "maze procedure," as is disclosed by Cox, J L et al. in "The surgical treatment of atrial fibrillation. I. Summary" Thoracic and Cardiovascular Surgery 101(3), pp. 402–405 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium.

The "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

While the "maze" procedure as reported by Cox and others has met some success in treating patients with atrial arrhythmia, its highly invasive methodology is believed to be prohibitive in most cases. However, these procedures have provided a guiding principle that mechanically isolating faulty cardiac tissue may successfully prevent atrial arrhythmia, and particularly atrial fibrillation caused by perpetually wandering reentrant wavelets or focal regions of arrhythmogenic conduction.

Success with surgical interventions through atrial segmentation, particularly with regard to the surgical "maze" procedure just described, has inspired the development of less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as those disclosed in U.S. Pat. No. 5,617,854 to Munsif, U.S. Pat. No. 4,898,591 to Jang et al., U.S. Pat. No. 5,487,385 to Avitall, and U.S. Pat. No. 5,582,609 to Swanson, the disclosures of which are incorporated herein by reference. The use of particular guiding sheath designs for use in ablation procedures in both the right and/or left atrial chambers are disclosed in U.S. Pat. Nos. 5,427,119, 5,497,119, 5,564,440, and 5,575,766 to Swartz et al., the disclosures of which are incorporated herein by reference. In addition, various energy delivery modalities have been disclosed for forming such atrial wall lesions, and include use of microwave, laser, and more commonly, radiofrequency energies to create conduction blocks along the cardiac tissue wall, as disclosed in WO 93/20767 to Stem et al., U.S. Pat. No. 5,104,393 to Isner et al., and U.S. Pat. No. 5,575,766 to Swartz et al, respectively, the disclosures of which are incorporated herein by reference.

In addition to attempting atrial wall segmentation with long linear lesions for treating atrial arrhythmia, ablation catheter devices and methods have also been disclosed that are intended to ablate arrhythmogenic tissue of the left-sided accessory pathways, such as those associated with the Wolff-Parkinson-White syndrome, through the wall of an adjacent region along the coronary sinus. For example, Fram et al., in "Feasibility of RF Powered Thermal Balloon Ablation of Atrioventricular Bypass Tracts via the Coronary Sinus: In vivo Canine Studies," PACE, Vol.18, p 1518–1530 (1995), disclose attempted thermal ablation of left-sided accessory pathways in Jo dogs using a balloon that is heated with bipolar radiofrequency electrodes positioned within the balloon. Additional examples of cardiac tissue ablation from the region of the coronary sinus for the purpose of treating particular types of cardiac arrhythmias are disclosed in: "Long-term effects of percutaneous laser balloon ablation from the canine coronary sinus", Schuger C D et al., Circulation (1992) 86:947–954; and "Percutaneous laser balloon coagulation of accessory pathways", McMath L P et al., Diagn Ther Cardiovasc Interven 1991; 1425:165–171.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways. One example of a focal ablation method intended to destroy and thereby treat focal arrhythmia originating from a pulmonary vein is disclosed by Haissaguerre, et al. in "Right and Left Atrial Radiofrequency Catheter Therapy of Paroxysmal Atrial Fibrillation" in Journal of Cardiovascular Electrophysiology 7(12), pp. 1132–1144 (1996). In another focal ablation example, Jais et al. in "A focal source of atrial fibrillation treated by discrete radiofrequency ablation" Circulation 95:572–576 (1997) applies an ablative technique to patients with paroxysmal arrhythmias originating from a focal source.

U.S. Pat. Nos. 6,024,740 and 6,117,101 disclose catheters for ablating a circumferential lesion in the pulmonary vein or other region. The catheters include a circumferential ablation element comprising an expandable balloon and an ablation element, such as an ultrasound transducer, coupled to the expandable balloon. The ablation element couples to the balloon's outer skin to ablate a circumferential path of tissue engaged to the balloon. This arrangement has been found effective for creating the desired circumferential ablation. However, it would be desirable to provide a mechanism to enhance stabilization of the ablation element in the pulmonary vein or other region. It would also be desirable to provide a mechanism for controlling the size and shape of the balloon to enhance the stabilization of the balloon and the contract with the tissue in the pulmonary vein. It would also be desirable to provide a mechanism for controlling the precise position of the ablation element once the catheter is positioned in the heart.

SUMMARY OF THE INVENTION

The present invention is directed to an improved catheter having a circumferential ablation element surrounded by an inflatable balloon that includes a mechanism for changing the shape of the balloon once expanded. The inventive catheter is particularly useful for treatment within a tubular region of or near the heart, e.g., a pulmonary vein, the coronary sinus, the superior vena cava, or the pulmonary outflow tract.

In one embodiment, the catheter comprises an elongated tubular catheter body having an outer wall, proximal and distal ends, and a lumen extending therethrough. The catheter also comprises a generally tubular inner support member having proximal and distal ends and a lumen extending therethrough. A proximal portion of the inner support member extends into the lumen of the catheter body, and a distal portion of the inner support member extends outside the catheter body. A circumferential ablation element, such as an ultrasound transducer, is mounted on the distal portion of the inner support member outside the catheter body. A moveable tube extends through the lumen of the inner support member and through the catheter body. The moveable tube is longitudinally moveable relative to the inner support member and catheter body and has a distal end that extends beyond the distal end of the inner support member. An inflatable balloon is provided generally in surrounding relation to the circumferential ablation element. The inflatable balloon has a proximal end attached, directly or indirectly, to the distal end of the catheter body and a distal end attached, directly or indirectly, to a portion of the moveable tube that extends beyond the distal end of the inner support member. Longitudinal movement of the moveable tube relative to the catheter body and inner support member causes movement of the distal end of the balloon relative to the proximal end of the balloon to thereby change the length and shape of the expanded balloon.

DESCRIPTION OF THE DRAWINGS

These and other features and advantages of the present invention will be better understood by reference to the following detailed description when considered in conjunction with the accompanying drawings wherein:

FIG. 1 is a side cross-sectional view of an embodiment of the catheter of the invention.

FIG. 2 is an enlarged detail view of the ablation assembly of the catheter of FIG. 2.

DETAILED DESCRIPTION

In an exemplary embodiment of the invention, there is provided a catheter for ablating a circumferential region of tissue, such as a pulmonary vein wall. As shown in FIG. 1, the catheter comprises an elongated catheter body 12 having proximal and distal ends, a circumferential ablation assembly 14 at the distal end of the catheter body, and a control handle 16 at the proximal end of the catheter body.

In the depicted embodiment, the catheter body 12 comprises an elongated tubular construction having one or more lumens extending therethrough. The catheter body 12 is flexible, i.e., bendable, but substantially non-compressible along its length. The catheter body 12 can be of any suitable construction and made of any suitable material, such as polyurethane or PEBAX. A presently preferred construction is a layered construction comprising a braided mesh of stainless steel imbedded between an outer layer of PEBAX and an inner layer of nylon. The braided mesh increases the torsional stiffness of the catheter body 12 so that, when the handle 16 is rotated, the distal end of the catheter will rotate in a corresponding manner. The outer diameter of the catheter body 12 is not critical, but preferably ranges from about 5 french to about 10 french, more preferably from about 7 French to about 9 French.

The useful length of the catheter, i.e., that portion that can be inserted into the body, can vary as desired. Preferably the useful length ranges from about 110 cm to about 130 cm.

In one more detailed construction, the proximal end of the catheter body 12 is adapted to be more stiff, preferably at least 30% more stiff, than the distal end of the catheter body. With this design, the proximal end is suitably adapted to provide push transmission to the distal end, while the distal end portion is suitably adapted to track through bending anatomy during in vivo delivery of the distal end portion of the device into the desired ablation region and can easily be deflected, as discussed further below.

Figure 3:
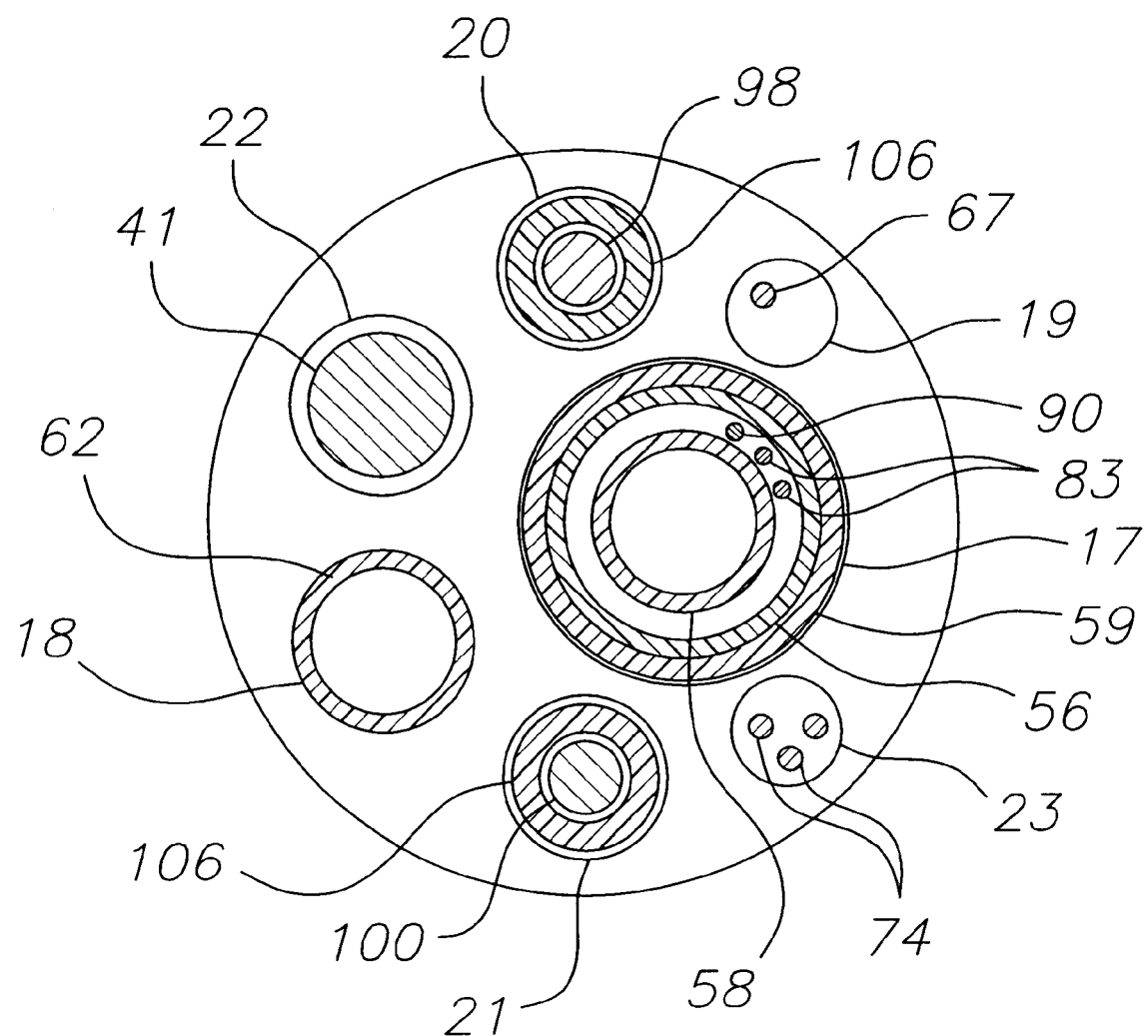
FIG. 3 is an end cross-sectional view of the distal region of the catheter body of FIG. 1 along line 3—3.

In a particularly preferred construction, the catheter body 12 comprises a proximal region 13 formed from a 70D PEBAX tubing and having a length ranging from about 100 cm to about 125 cm, and a distal region 15 formed from a 55D PEBAX tubing and having a length ranging from about 1 cm to about 12 cm, preferably from about 5 cm to about 6 cm. The proximal region 13 has a single central lumen extending therethrough, and the distal region 15 has seven lumens extending therethrough, as depicted in FIG. 3. The seven lumens include a relatively large guidewire lumen 17, an inflation lumen 18, a transducer thermocouple lumen 19, a first puller wire lumen 20, a second puller wire lumen 21, a coaxial cable lumen 22, and a balloon thermocouple lumen 23. The number and sizes of the lumens in the catheter body 12 can vary as desired depending on the components that extend through the catheter body. Other modifications to the size and number of lumens, as well as to the arrangement of components in the lumens, are within the scope of the invention.

Figure 4:
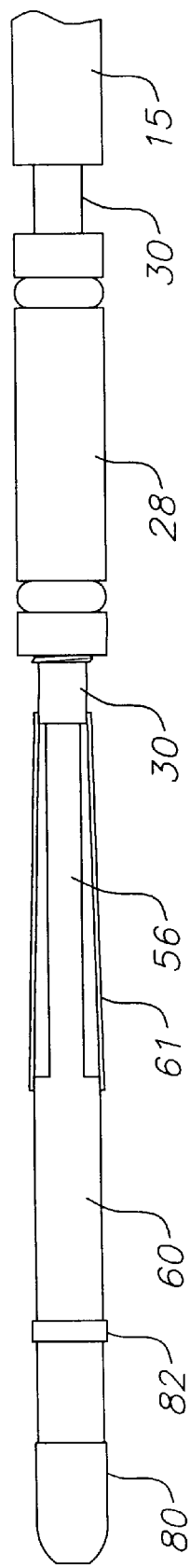
FIG. 4 is a side schematic view of the transducer and distal end of the catheter of FIG. 1.

The circumferential ablation assembly 14, which is mounted at the distal end of the catheter body 12, is shown in detail in FIGS. 2 and 4. The ablation assembly comprises an expandable balloon 26, a circumferential ablation element 28 that is acoustically coupled to the expandable balloon, and an inner support member 30.

The inner support member 30 preferably comprises a biocompatible plastic, such as polyimide, polyurethane or PEBAX. The inner support member 30 has a proximal end that extends a short distance (e.g., about 5 mm to about 8 mm) into the guidewire lumen 17 of the distal region 15 of the catheter body 12 and a distal end that extends slightly beyond the distal end of the ablation element 28.

In the depicted embodiment, the circumferential ablation element 28 takes the form of an annular ultrasonic transducer. The annular ultrasonic transducer 28 has a unitary cylindrical shape with a hollow interior (i.e., is tubular shaped). However, the transducer can have a generally annular shape and be formed of a plurality of segments. For instance, the transducer can be formed by a plurality of tube sectors that together form an annular shape. The tube sectors can also be of sufficient arc lengths so as when joined together, the sectors assembly forms a "clover-leaf" shape. This shape is believed to provide overlap in heated regions between adjacent elements. The generally annular shape can also be formed by a plurality of planar transducer segments which are arranged in a polygon shape (e.g., hexagon). In addition, although in the illustrated embodiment the ultrasonic transducer comprises a single transducer element, the transducer can be formed of a multi-element array.

The length of the transducer 28 (or multi-element array of transducer elements that forms the transducer) desirably is selected for a given clinical application. In connection with forming circumferential condition blocks in cardiac or pulmonary vein wall tissue, the transducer length preferably ranges from about 2 mm to about 10 mm, more preferably from about 5 mm to about 10 mm. A transducer accordingly sized is believed to form a lesion of a width sufficient to ensure the integrity of the formed conductive block without undue tissue ablation. For other applications, however, the length can be significantly longer.

Likewise, the outer diameter of the transducer 28 desirably is selected to account for delivery through a particular access path (e.g., percutaneously or transeptally), for proper placement and location within a particular body space, and for achieving a desired ablation effect. In a preferred application within or near the pulmonary vein ostium, the transducer 28 preferably has an outer diameter ranging from about 1.8 mm to about 2.5 mm or greater. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer 28 may have an outer diameter ranging from about 1 mm to about 2 cm, depending on the application.

The transducer 28 has a thickness selected to produce a desired operating frequency. The operating frequency will vary depending upon clinical needs, such as the tolerable outer diameter of the ablation and the depth of heating, as well as upon the size of the transducer as limited by the delivery path and the size of the target site. The transducer 28 in the illustrated embodiment preferably operates at a frequency ranging from about 5 MHz to about 20 MHz, and more preferably from about 7 MHz to about 10 MHz. Thus, for example, the transducer can have a thickness of approximately 0.3 mm for an operating frequency of about 7 MHz (i.e., a thickness generally equal to half the wavelength associated with the desired operating frequency).

Figure 4A:
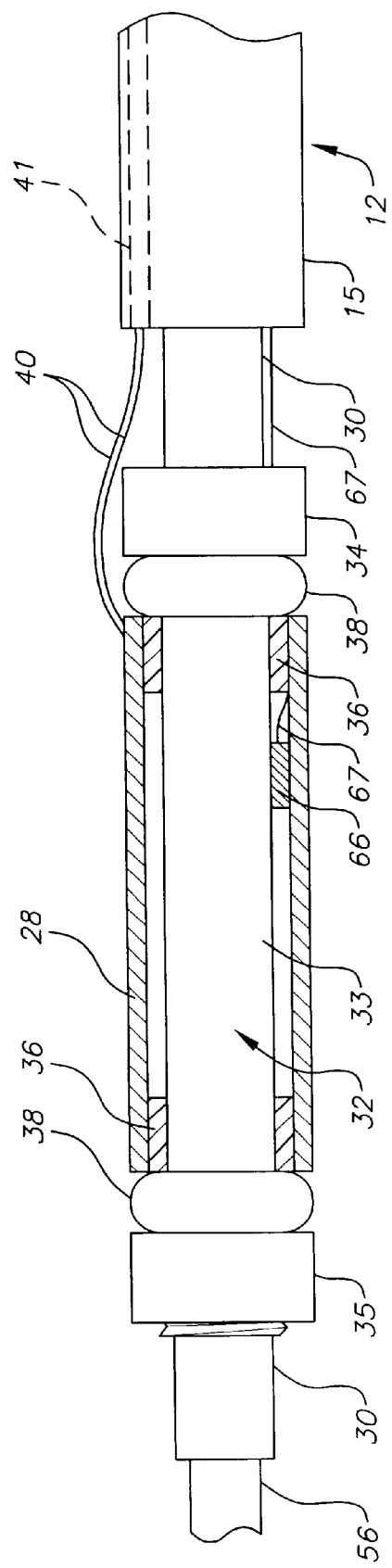
FIG. 4A is a side cross-sectional view of the transducer shown in FIG. 4.

A preferred arrangement for mounting the transducer 28 comprises a transducer mount 32 provided over the inner support member 30, as shown in detail in FIG. 4A. The transducer mount 32 comprises an elongated cylindrical body 33 with a lumen (not shown) extending therethrough, a permanent proximal end cap 34 and a detachable, threaded distal end cap 35. The transducer mount 32 preferably comprises stainless steel. The inner support member 30 extends through the lumen of the cylindrical body 33 and is attached to the transducer mount 32 with silicone glue or the like.

The transducer 28 is mounted in surrounding relation to the cylindrical body 33 of the transducer mount 32. Two short pieces of silicone tubing 36 or the like are provided between the transducer mount 32 and the transducer 28 at the proximal and distal ends of the transducer. This arrangement provides an air backing for the transducer 28 to produce more energy and to enhance energy distribution uniformity, as is known in the art. The pieces of silicone tubing 36 also serve to evenly center and support the transducer 28 on the transducer mount 32. Two O-rings 38 are provided over the cylindrical body 33 of the transducer mount 33, one between the proximal end of the transducer 28 and the proximal end cap 34, and the other between the distal end of the transducer and the distal end cap 35. The O-rings 38 are preferably made of silicone and serve as seals to prevent the balloon inflation fluid, described further below, from leaking inside the transducer 28 or transducer mount 32.

The transducer 28 is vibrated across the wall thickness and to radiate collimated acoustic energy in the radial direction. For this purpose, two electrical transducer leads 40 are electrically coupled to the transducer 28, preferably by solder or the like. In a preferred embodiment, the electrical leads each comprises a 4 to 8 mil (0.004 to 0.008 inch diameter) silver wire or the like. The proximal ends of the electrical transducer leads 40 are electrically connected to wires in a coaxial cable 41, which extends through the coaxial cable lumen 22 of the distal region 15 of the catheter body 12. The proximal end of the coaxial cable 41 extends out through the proximal end of the control handle 16. A suitable coaxial cable connector 42 mounted on the proximal end of the coaxial cable 41 connects the coaxial cable to a source of ultrasound energy (not shown), such as an ultrasonic actuator. Other configurations for the transducer leads 40 are contemplated within the scope of the invention. Detailed examples of alternative transducer configurations and support structures are disclosed in U.S. Pat. Nos. 6,117,101 and 5,620,479, the disclosures of which are incorporated herein by reference.

The ultrasonic actuator generates alternating current to power the transducer. The ultrasonic actuator drives the transducer at frequencies ranging from about 5 to about 20 MHz, and preferably for the present application ranging from about 7 MHz to about 10 MHz. In addition, the ultrasonic driver can modulate the driving frequencies and/or vary power to smooth or unify the produced collimated ultrasonic beam. For instance, the function generator of the ultrasonic actuator (840) can drive the transducer at frequencies ranging from about 6.8 MHz to about 7.2 MHz by continuously or discretely sweeping between these frequencies.

The arrangement of the expandable balloon 26 is shown in FIG. 2. The balloon has a primary region 50, which is generally coaxially disposed over the inner support member 30, and proximal and distal neck regions 52 and 54.

Figure 4B:
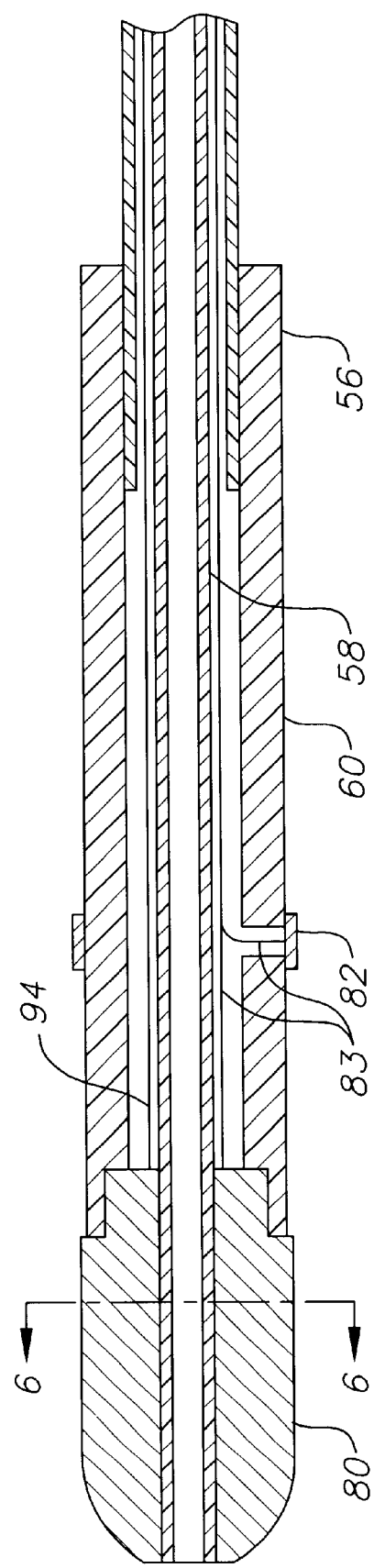
FIG. 4B is a side cross-sectional view of the distal tube shown in FIG. 4.

A mechanism is provided for changing the shape of the expanded balloon 26. As shown in FIGS. 4 and 4B, two moveable tubes, an outer moveable tube 56 and an inner moveable tube 58, extend through the inner support member 30, the guidewire lumen 17 in the distal 10 region 15 of the catheter body 12, the single lumen of the catheter body, and into the control handle 16. The distal ends of the moveable tubes 56 and 58 are both anchored to a distal tubing 60 that is distal to the transducer 28 and the distal end of the inner support member 30, as shown best in FIG. 4B. The proximal ends of the moveable tubes 56 and 58 extend into the control handle 16, where the outer moveable tube 56 terminates. The inner moveable tube 58 extends out the proximal end of the control handle 16 and is anchored to a mechanism attached to the control handle for causing longitudinal movement of the moveable tubes relative to the catheter body 12 and inner support member 30, as described further below. The moveable tubes 56 and 58 are made of any suitable biocompatible material, and preferably polyimide. The distal tubing 60 is made of any suitable biocompatible material, and preferably a non-conductive material such as polyurethane.

The proximal neck region 52 of the balloon 26 is disposed about and attached to the distal region 15 of the catheter body 12, preferably using glue or heat. The distal neck region 54 of the balloon is disposed about and attached to the distal end of the distal tubing 60, preferably using glue or heat. Longitudinal movement of the moveable tubes 56 and 58 relative to the catheter body 12 and transducer 28 causes the distal neck region 54 of the balloon to be pulled relative to the proximal neck region 52, thereby changing the shape of the expanded balloon. This relative movement can be performed before, during or after expansion of the balloon.

According to the above-described arrangement, a fluid tight interior chamber is formed within the expandable balloon 26. This interior chamber is fluidly coupled to a pressurizeable fluid source (not shown) via an inflation tubing 62 that extends through the catheter body 12 and has its distal end anchored in the proximal end of the inflation lumen 18 of the distal region 15 of the catheter body 12. The inflation tubing 62 extends out through the proximal end of the control handle 16 and has a suitable luer hub 64 mounted on its proximal end for introducing fluid into the inflation tubing and balloon. The expanded balloon 26 functions to stabilize the ablation assembly within the region to be ablated, and particularly in a tubular region of or near the heart, such as the pulmonary vein. The coaxial cable lumen 22 also communicates with the interior chamber of the expandable balloon 26 so that the ultrasound transducer 28, which is positioned within that chamber and over the inner support member 30, can be electrically coupled to an ultrasound actuator via the coaxial cable 41 extending through the coaxial cable lumen, as discussed above.

To change the shape of the balloon 26, the moveable tubes 56 and 58, along with the distal tubing 60 on which the distal end of the balloon is mounted, are moved longitudinally relative to the catheter body 12. The moveable tubes 56 and 58 extend through the guidewire lumen 17 and into the control handle 16, with the inner moveable tube 58 extending out the control handle where its proximal end is connected to a luer hub 48. A portion of the inner moveable tube 58 outside the control handle 16 is contained within and anchored to a housing 63, preferably made of plastic. The housing 63 is moveable relative to the catheter body 12 and control handle 16. By this design, longitudinal movement of the housing 63 relative to the control handle 16 and catheter body 12 causes longitudinal movement of the moveable tubes 56 and 58 (which are attached to each other at their distal ends) relative to the catheter body and inner support member 30, thereby moving the distal neck region 54 of the balloon 26 toward or away from the proximal neck region 52 of the balloon and thus constricting or elongating the balloon.

Additionally, an elastic tubing 61 is provided to prevent fluid from entering the catheter body 12 between the outer moveable tube 56 and the distal end of the inner support member 30. As shown in FIG. 4, the elastic tubing 61 has a proximal end glued or otherwise bonded to the distal end of the inner support member 30 and a distal end bonded to the proximal end of the distal tube 60. The elastic tubing 61 is made of an elastic material, preferably silicone, so that the elastic tubing will stretch and return to its original shape when the moveable tubes 56 and 58 are moved relative to the inner support member 30 and catheter body 12.

As noted above, the proximal end of the inner support member 30 extends a short distance into the guidewire lumen 17 of the distal region 15 of the catheter body 12. The proximal end of the inner support member 30 fits tightly within the guidewire lumen 17 to seal the junction of the inner support and the guidewire lumen. An elongated plastic tubing 59, preferably made of polyimide, having a size similar to the inner support member 30, is provided and has its distal end mounted in the proximal end of the guidewire lumen 17. The elongated plastic tubing 59 extends through the catheter body 12 and into the control handle 16 in surrounding relation to the moveable tubes 56 and 58. The elongated plastic tubing 59 also fits tightly within the guidewire lumen 17 to create a seal between the guidewire lumen and the elongated plastic tubing.

The expandable balloon 26 may be constructed from a variety of known materials, although the balloon preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, silicone, latex, and low durometer polyurethane (for example, a durometer of about 80A). The use of a polyurethane balloon is particularly suitable when it is desired to change the shape of the expanded balloon. In addition or in the alternative to constructing the balloon of highly compliant material, the balloon can be formed to have a predefined fully inflated shape (i.e., be pre-shaped) to generally match the anatomic shape of the body lumen in which the balloon is to be inflated. For instance, the balloon can have a distally tapering shape to generally match the shape of a pulmonary vein ostium and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

In a particularly preferred embodiment, the balloon is constructed to exhibit at least 300% expansion at 3 atmospheres of pressure, and more preferably to exhibit at least 400% expansion at that pressure. The term "expansion" refers to the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to the change in diameter that is attributable to the material compliance in a stress strain relationship. In one embodiment, the balloon is adapted to expand under a normal range of pressure such that its outer diameter may be adjusted from a radially collapsed position of about 5 millimeters to a radially expanded position of about 2.5 centimeters (having approximately a 500% expansion ratio).

The transducer 28 may be electrically and mechanically isolated from the interior of the balloon 26. Any of a variety of coatings, sheaths, sealants, tubings and the like may be suitable for this purpose, such as those described in U.S. Pat. Nos. 5,620,479 and 5,606,974. For example, a conventional, flexible, acoustically compatible and medical grade epoxy may be applied over the transducer 28. The epoxy may be, for example, Epotek 301, Epotek 310, which is available commercially from Epoxy Technology, or Tracon FDA-8. In addition, a conventional sealant (not shown), such as General Electric Silicon II gasket glue and sealant, may be applied at the proximal and distal ends of the transducer 28 around the exposed portions of the inner support member 30 and transducer leads 40 to seal the space between the transducer and the inner support member at these locations.

The ultrasound transducer 28 of the present embodiment sonically couples with the outer skin of the balloon 26 in a manner that forms a circumferential conduction block in a pulmonary vein. Initially, the ultrasound transducer 28 is believed to emit its energy in a circumferential pattern that is highly collimated along the transducer's length relative to its longitudinal axis. The circumferential band therefore maintains its width and circumferential pattern over an appreciable range of diameters away from the source at the transducer. Also, the balloon 26 is preferably inflated with fluid (not shown) that is relatively ultrasonically transparent, such as, for example, non-ionic saline or degassed water. In a preferred embodiment, the inflation fluid comprises a radiopaque dye, such as Omnipaque 360 (commercially available from Nycomed), and more preferably a 70:30 mixture of saline and non-ionic contrast solution, so that the position of the transducer can be determined using fluoroscopy. By actuating the transducer while the balloon is inflated, the circumferential band of energy is allowed to translate through the inflation fluid and ultimately sonically couple with a circumferential band of balloon skin that circumscribes the balloon. Moreover, the circumferential band of balloon skin material may also be further engaged along a circumferential path of tissue that circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated. The energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

Alternatively, the balloon can be elongated using the moveable tubes 56 and 58 as described above, which can advantageously increase the surface area of the balloon that is in contact with the tissue to be ablated. The use of an adjustable balloon allows the user to adjust the balloon for certain diameters and lengths to accommodate patient anatomy.

In one particular balloon-transducer combination, the ultrasound transducer preferably has a length such that the ultrasonically coupled band of the balloon skin, having a similar length according to the collimated electrical signal, is shorter than the working length of the balloon. According to this aspect of the relationship, the transducer is adapted as a circumferential ablation element that is coupled to the balloon to form an ablation element along a circumferential band of the balloon, therefore forming a circumferential ablation element band that circumscribes the balloon. Preferably, the transducer has a length that is less than two-thirds the working length of the balloon, and more preferably less than one-half the working length of balloon—and hence shorter than a longitudinal length of the engagement area between the balloon and the wall of the body space (e.g., pulmonary vein ostium)—and by generally centering the transducer within the balloon's working length, the transducer operates in a field isolated from the blood pool. A generally equatorial position of the transducer relative to the ends of the balloon's working length also assists in the isolation of the transducer from the blood pool. It is believed that the transducer placement according to this arrangement may be preventative of thrombus formation that might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the catheter body 12 may include an additional radiopaque marker or markers (not shown) to identify the location of the transducer 28 in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The use and placement of a suitable radiopaque marker for use in the present invention is described in U.S. Pat. No. 6,117,101, the disclosure of which is incorporated herein by reference.

If desired, one or more temperature sensing devices are provided for monitoring the temperature on and around the ablation assembly 14. For example, temperature sensing devices, such as thermocouples, can be used for measuring the temperature of the inflation fluid inside the balloon 26, for measuring the temperature of the transducer 28, and/or for measuring the temperature of the tissue during ablation.

In the depicted embodiment, a transducer thermocouple 66 is provided between the transducer 28 and the transducer mount 32 and held in place by glue or the like. The wire 67 for the transducer thermocouple 66 extends between the proximal piece of silicone tubing 36 and the transducer mount, through the transducer thermocouple lumen 19 of the distal region 15 of the catheter body 12, and out the proximal end of the control handle 16, where it passes through a protective tubing 68 and is attached at its proximal end to a suitable thermocouple connector 69 for electrically connecting the thermocouple to an appropriate monitoring device (not shown).

Figure 5:
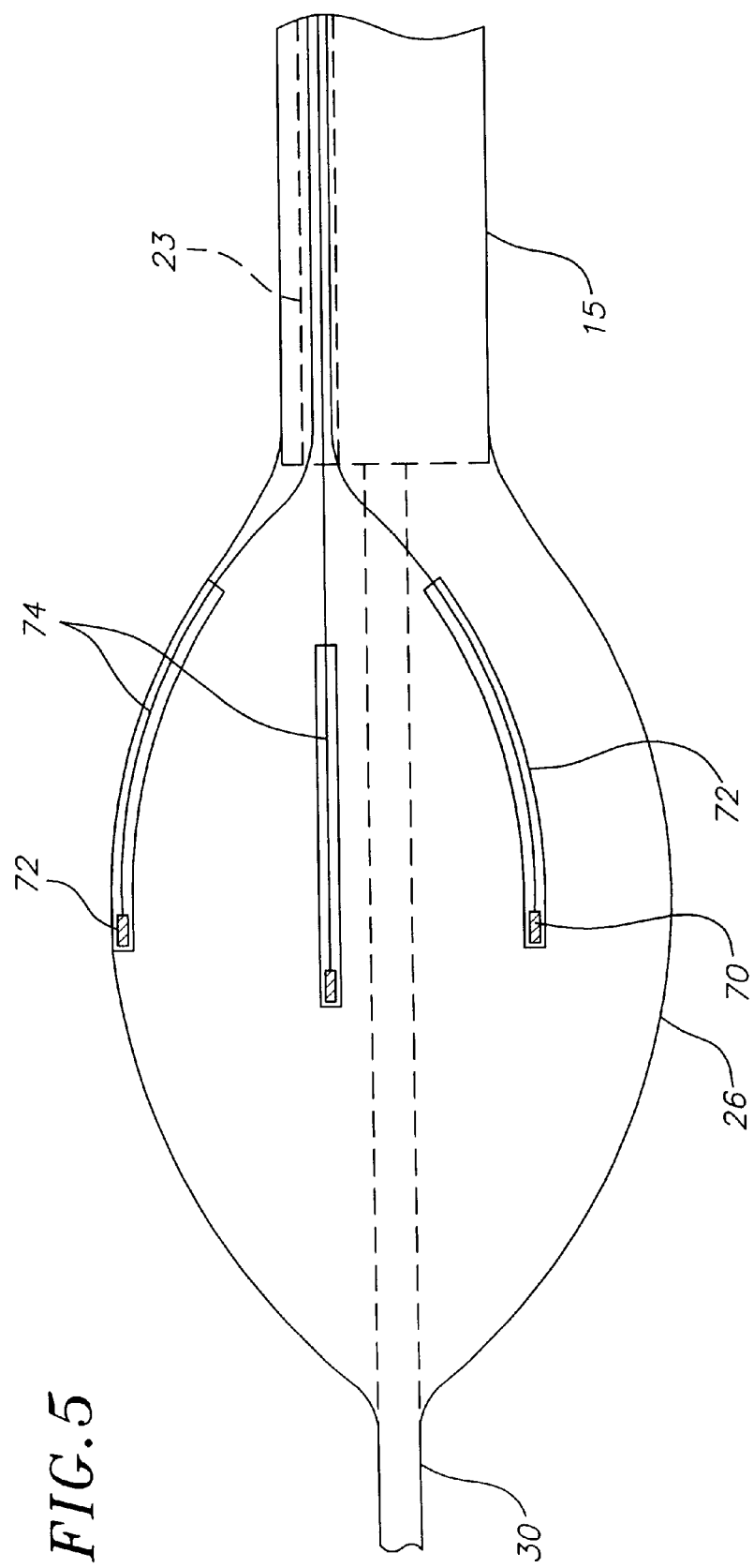
FIG. 5 is a side schematic view of an expanded balloon showing the position of the thermocouples in the balloon.

Additionally, three balloon thermocouples 70 are provided and attached to the inside the balloon 26. As shown in FIG. 5, the three balloon thermocouples 70 are provided approximately evenly around the circumference of the balloon (preferably 120° apart) and at three different locations along the length of the balloon. Each balloon thermocouple 70 is mounted within a corresponding tube 72 that is bonded to the interior of the balloon 26 and preferably made of the same material as the balloon. The balloon thermocouple wires 74 extend through the balloon thermocouple lumen 23 of the distal region 15 of the catheter body 12, and out the proximal end of the control handle 16, where, like the transducer thermocouple wire 67, they pass through the protective tubing 68 and are attached at their proximal ends to the thermocouple connector 69.

The distal tubing 60, to which the distal end of the balloon 26 is anchored, preferably also carries one or more electrodes and/or temperature sensors for mapping, recording and/or ablating. In the depicted embodiment, a tip electrode 80 is mounted on the distal end of the distal tubing 60, and a ring electrode 82 is mounted on the distal tubing proximal to the tip electrode. The tip electrode 80 and ring electrode 82 can be made of any suitable material, and are preferably machined from platinum-iridium bar (90% platinum/10% iridium).

The tip electrode 80 and ring electrode 82 are each connected to a separate lead wire 83. The lead wires 83 extend through the distal tubing 60, between the outer moveable tube 56 and the inner moveable tube 58, inside the inner support member 30 (where they run through the transducer 28), and through the catheter body 12, still between the outer moveable tube and the inner moveable tube. When the outer moveable tube 56 terminates in the control handle 16, as described above, the lead wires 83 extend through a protective sheath 86 out the proximal end of the control handle 16 and are connected at their proximal ends to a suitable lead wire connector 85, which is connected to an appropriate monitoring device, recording device and/or source of ablation energy (not shown).

Figure 6:
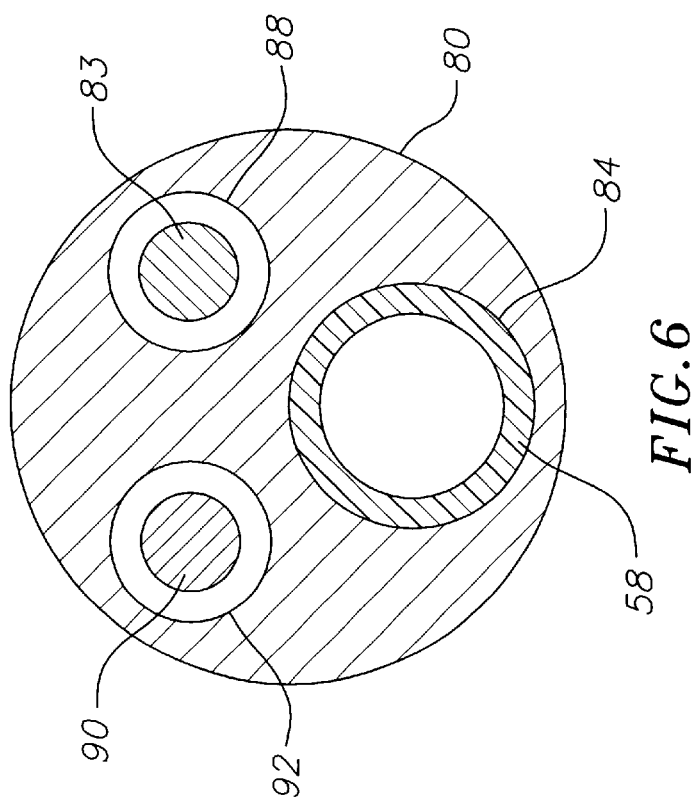
FIG. 6 is an end cross-sectional view of the tip electrode of FIG. 4B along line 6—6.

The lead wires 83 are attached to the tip electrode 80 and ring electrode 82 by any conventional technique. Connection of a lead wire 83 to the tip electrode 80 is accomplished, for example, by soldering the lead wire 83 into a first blind hole 88 in the tip electrode, as shown in FIG. 6.

Connection of a lead wire 83 to the ring electrode 82 is preferably accomplished by first making a small hole through the distal tubing 60. Such a hole can be created, for example, by inserting a needle through the tube 60 and heating the needle sufficiently to form a permanent hole. A lead wire 83 is then drawn through the hole by using a microhook or the like. The end of the lead wire 83 is then stripped of any coating and soldered or welded to the underside of the ring electrode 82, which is then slid into position over the hole and fixed in place with polyurethane glue or the like.

In the depicted embodiment, a thermocouple 90 (or other temperature sensor) is provided for monitoring the temperature of the tip electrode 80. The thermocouple 90 is mounted within a second blind hole 92 in the tip electrode and held in place using glue, solder, weld or any other suitable method. The wire 94 for the thermocouple extends with the lead wires 83 through the distal tubing 60, between the outer moveable tube 56 and the inner moveable tube 58, inside the inner support member 30 (where they run through the transducer 28), and through the catheter body 12, still between the outer moveable tube and the inner moveable tube. The thermocouple wire 94 extends through the protective sheath 68 with the lead wires 83 out the proximal end of the control handle 16 and is connected at its proximal end to the lead wire connector 69.

The tip electrode 80 also includes a guidewire passage 84, which is open at the distal end of the tip electrode. The inner moveable tube 58 extends into and is mounted in the guidewire passage 84, preferably by glue or the like. The outer moveable tube 56 does not extend into the tip electrode, but has its distal end mounted closer to the proximal end of the distal tubing 60, preferably with glue or the like, as best shown in FIG. 4B. The inner moveable tube 58 thus defines a passage through which a guidewire, second catheter or infusion fluid can pass through the entire length of the catheter. The moveable tubes 56 and 58 are preferably bonded together at their proximal ends with glue or the like and extend out the proximal end of the control handle 16. As noted above, a luer hub 48 is provided on the proximal end of the joined tubes 56 and 58 for introduction of a guidewire or fluid through the inner tube 58. It has been found that the use of two moveable tubes is desirable to provide enhanced support, although the two tubes can be replaced with a single tube if desired.

As would be recognized by one skilled in the art, other arrangements of electrodes for mapping or ablating can be provided on the distal tubing 60. For example, a generally circular electrode array can be included on the distal end of the distal tubing, which is useful not only for mapping or ablating, but also for stabilizing the distal end of the catheter within a tubular region of or near the heart. Such an electrode array is described in U.S. patent application Ser. No. 10/201,052, entitled "Ablation Catheter Having Stabilizing Array," the disclosure of which is incorporated herein by reference. Alternatively, the distal tubing 60 can carry an expandable basket-shaped arrangement having a plurality of spines, preferably including one or more electrodes on each spine. Such structures are describes in U.S. Pat. Nos. 5,411,025, 5,772,590, 5,628,313, 6,292,695, and U.S. patent application Ser. No. 10/017,029, filed Dec. 14, 2001, entitled "Basket Catheter with Multiple Location Sensors," the disclosures of which are incorporated herein by reference.

Figure 7:
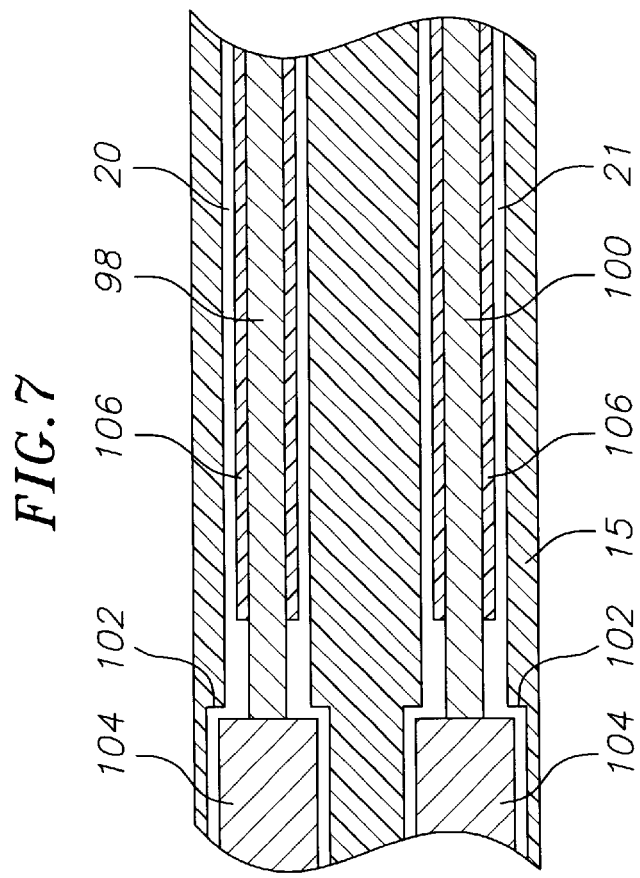
FIG. 7 is a side cross-sectional view of the distal region of the catheter body showing how the puller wires are anchored.

First and second puller wires 98 and 100 are provided for deflection of the catheter body 12 proximal to the ablation assembly 14. The first puller wire 98 extends through the first puller wire lumen 20 of the distal region 15, and the second puller wire extends through the second puller wire lumen 21. Both puller wire lumens are preferably off-axis lumens. The puller wires 98 and 100 are anchored at their distal ends in the distal region 15 of the catheter body 12. FIG. 7 depicts a preferred arrangement for anchoring the puller wires 98 and 100. The distal ends of the first and second lumens 20 and 21 each contain a small step 102. An anchor 104 is mounted on the distal end of each of the first and second puller wires 98 and 100. Each anchor 104 preferably comprises a piece of hypodermic stock or stainless steel tubing crimped onto the distal end of its corresponding puller wire. The anchors 104 are sized so that the steps 102 prevent the anchors from being pulled proximally into the first and second lumens 20 and 21. Any other suitable arrangement for anchoring the puller wires 98 and 100 to the catheter body 12 can also be used in accordance with the invention. The distal end of each puller wire 98 and 100 is surrounded by a plastic, preferably Teflon®, puller wire sheath 106, which prevents the corresponding puller wire from cutting into the wall of the distal region 15 of the catheter body 12 when it is deflected. Each puller wire sheath 106 preferably has a length of approximately 3 cm.

Each puller wire 98 and 100 is made of any suitable metal, such as stainless steel or Nitinol, and is preferably coated with Teflon® or the like. The coating imparts lubricity to the puller wires 98 and 100. Each puller wire 98 and 100 preferably has a diameter ranging from about 0.006 to about 0.010 inch. In a preferred embodiment, two compression coils (not shown) are situated within the single lumen of the catheter body 12, each in surrounding relation to a corresponding puller wire 98 and 100. Each compression coils is made of any suitable metal, preferably stainless steel, and is tightly wound on itself to provide flexibility, i.e., bending, but to resist compression. An example of a catheter construction including a puller wire and compression coil suitable for use in the present invention is disclosed in U.S. Pat. No. 6,371,955, the disclosure of which is incorporated here coil is preferably enclosed with a protective sleeve (not shown) within the single lumen of the catheter body 12 to avoid other components within the single lumen from getting caught in or intertwined with the compression coils.

Longitudinal movement of a puller wire 98 or 100 relative to the catheter body 12, which results in deflection of the distal end of the catheter body in the direction of the side of the catheter to which that puller wire is anchored, is accomplished by suitable manipulation of the control handle 16. Examples of suitable bidirectional control handles for use in manipulating two puller wires according to the present invention are disclosed, for example, in U.S. Pat. Nos. 6,123,699, 6,171,277, 6,183,435, 6,183,463, 6,198,974, 6,210,407, and 6,267,746, and in U.S. application Ser. No. 09/546,301, entitled "Single Gear Drive Bidirectional Control Handle for Steerable Catheter," the disclosures of which are incorporated herein by reference.

If deflection of the distal tubing 60 is desired, a puller wire (not shown) can be provided that extends through a lumen in the catheter body 12 and through the inner support member 30, for example, in a manner similar to the electrode lead wires 83. The distal end of the puller wire is anchored at or near the proximal end of the distal tubing 60 in a manner similar to that described above or any other suitable manner. The puller wire can be manipulated using any suitable control handle, such as those referenced above.

In an alternative embodiment, a mechanism is provided for longitudinally moving the transducer 28 relative to the catheter body 12. Such movement of the transducer can be desirable to properly position the transducer at the ostium. In this embodiment, the inner support member 30 extends through the catheter body 12 and into the control handle 16, and the elongated plastic tubing 59 can be eliminated. The proximal end of the inner support member 30 is attached to a moveable member within the control handle to cause longitudinal movement of the inner support member 30 (and thus the transducer mounted thereon) relative to the catheter body 12. The inner support member 30 also moves relative to the moveable tubes 56 and 58 so that the transducer 28 can be moved relative to the balloon 26. A suitable control handle mechanism for affecting longitudinal movement of the inner support member 30 comprises a rotatable sleeve (not shown) mounted on the outside of the handle. The inner surface of the rotatable sleeve contains teeth that interact with a longitudinally moveable gear to which the proximal end of the inner support member is anchored. By this design, rotation of the rotatable sleeve causes longitudinal movement of the gear and inner support member, thereby moving the transducer 28 relative to the catheter body. Such a design, which can be incorporated into a bidirectional control handle such as those referenced above, is described in U.S. patent application Ser. No. 10/040,981, entitled "Dual-Function Catheter Handle," the disclosure of which is incorporated herein by reference.

In a preferred method in accordance with the invention, the circumferential ablation assembly is positioned at an ablation region, preferably along a tubular region of or near the heart, more preferably along the pulmonary vein, and thereafter a continuous circumferential region of tissue at the ablation region is ablated. The circumferential ablation assembly is preferably introduced into a pulmonary vein of the left atrium according to a transeptal access method. This method generally involves accessing the right venous system using the "Seldinger" technique, whereby a peripheral vein (such as the femoral vein) is punctured with a needle. The puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brochenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

Other left atrial access methods may be suitable substitutes for using the circumferential ablation device assembly of the present invention. In one alternative, a "retrograde" approach may be used, wherein the guiding catheter is advanced into the left atrium from the arterial system. In this variation, the Seldinger technique is employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Subsequent to transeptal introduction of the guiding catheter into the left atrium, a guidewire is advanced into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) that is coaxial within the guiding catheter, such as, for example, by using one of the directional catheters disclosed in U.S. Pat. No. 5,575,766, the disclosure of which is incorporated herein by reference. Alternatively, the guidewire may have sufficient stiffness and maneuverability in the left atrial cavity to unitarily subselect the desired pulmonary vein distally of the guiding catheter seated at the fossa ovalis.

Suitable guidewire designs for use in the catheter of the present invention may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010" to 0.035" are particularly suitable. In cases where the guidewire is used to bridge the atrium from the guiding catheter at the fossa ovalis, and where no other sub-selective guiding catheters are used, guidewires having an outer diameter ranging from 0.018" to 0.035" may be required. It is believed that guidewires within this size range may be required to provide sufficient stiffness and maneuverability in order to allow for guidewire control and to prevent undesirable guidewire prolapsing within the relatively open atrial cavity.

The distal end of the catheter is introduced over the guidewire and into the pulmonary vein. The circumferential ablation assembly is positioned at an ablation region of the pulmonary vein where the circumferential conduction block is to be desirably formed.

Once the ablation assembly is generally positioned at a desired location within the pulmonary vein or vein ostium, the pressurized fluid source inflates the balloon to engage the lumenal surface of the pulmonary vein ostium. To affect proper stabilization and contact with the tissue inside the pulmonary vein, the balloon can be elongated before, during or after the inflation of the balloon with the pressurized fluid by manipulating the moveable tubes, as described above.

Proper location of the ablation, and thus proper placement of the transducer, is important to prevent reoccurance of atrial fibrillation. The preferred location for ablation is as ostial as possible. Accordingly, to the extent necessary, the location of the transducer can be fine-tuned by longitudinally moving the transducer relative to the inflated balloon and catheter body, as described above.

Once properly positioned, the ultrasonic driver is energized to drive the transducer. Driving the ultrasonic transducer at 20 acoustical watts at an operating frequency of 7 megahertz can form a sufficiently sized lesion circumferentially about the pulmonary vein ostium in a relatively short period of time (e.g., 1 to 4 minutes or less).

The control level of energy can be delivered, then tested for lesion formation with a test stimulus in the pulmonary vein. A preferred method for determining whether the ablation created sufficient entrance and exit block is to pace with a catheter in the coronary sinus and use electrodes on the stabilization assembly to confirm no capture. Alternatively, one or more stabilization assembly electrodes can be used for pacing to confirm that the wavefront cannot pass to a second catheter outside the pulmonary vein, such as in the coronary sinus or left atrium. Other suitable techniques would be known to one skilled in the art. The circumferential ablation assembly may also include feedback control using, for example, one or more thermocouples provided on or around the ablation assembly. Monitoring temperature at this location provides indicia for the progression of the lesion. This feedback feature may be used in addition to or in the alternative to the multi-step procedure described above. Therefore, the procedure may involve ablation at a first energy level in time, then a check for the effective conductive block provided by the resulting lesion, and then subsequent ablations and testing until a complete conductive block is formed.

The circumferential ablation device can also include additional mechanisms to control the depth of heating. For instance, the catheter body can include an additional lumen (not shown) that is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon can thus act as a heat sink to conduct away some of the heat from the targeted tissue and maintain the tissue below a desired temperature (e.g., 90° C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that fluids such as vegetable oil, silicone oil and the like are suitable for this application.

Uniform heating can also be enhanced by rotating the transducer 26 within the balloon 26. For this purpose, the inner support member 30, on which the transducer 28 is mounted, may be rotatable relative to the catheter body 12 and rotated using a suitable control handle, such as those referenced above.

In the above-described embodiment, the ultrasonic transducer has an annular shape so as to emit ultrasonic energy around the entire circumference of the balloon. The present circumferential ablation device, however, can emit a collimated beam of ultrasonic energy in a specific angular exposure. For instance, the transducer can be configured to have only a single active sector (e.g., 180 degree exposure). The transducer also have a planar shape. By rotating the catheter body, the transducer can be swept through 360 degrees in order to form a circumferential ablation. For this purpose, the transducer may be mounted on a torquible member, in the manner described above.

The circumferential ablation element has been described primarily as an annular ultrasonic transducer. However, other circumferential ablation elements can be used in connection with the invention, such as those described in U.S. Pat. No. 6,117,101, the entire disclosure of which is incorporated herein by reference.

The preceding description has been presented with reference to presently preferred embodiments of the invention.

Workers skilled in the art and technology to which this invention pertains will appreciate that alterations and changes in the described structures and methods may be practiced without meaningfully departing from the principal, spirit and scope of this invention.

Accordingly, the foregoing description should not be read as pertaining only to the precise structures and methods described and illustrated in the accompanying drawings, but rather should be read consistent with and as support to the following claims which are to have their fullest and fair scope.

What is claimed is:

1. A circumferential ablation catheter comprising:

an elongated tubular catheter body having an outer wall, proximal and distal ends, and a lumen extending therethrough;

a generally tubular inner support member having proximal and distal ends and a lumen extending therethrough, wherein a proximal portion of the inner support member extends into the lumen of the catheter body and a distal portion of the inner support member extends outside the catheter body;

a circumferential ablation element mounted on the distal portion of the inner support member outside the catheter body;

a moveable tube extending through the lumen of the inner support member and through the catheter body, the moveable tube being longitudinally moveable relative to the inner support member and catheter body and having a distal end extending beyond the distal end of the inner support member; and an inflatable balloon provided generally in surrounding relation to the circumferential ablation element, the inflatable balloon having a proximal end attached to the distal end of the catheter body and a distal end attached to a portion of the moveable tube that extends beyond the distal end of the inner support member;

wherein longitudinal movement of the moveable tube relative to the catheter body and inner support member causes movement of the distal end of the balloon relative to the proximal end of the balloon to thereby change the length of the balloon.

2. A catheter according to claim 1, wherein the circumferential ablation element comprises an ultrasound ablation element, wherein the ultrasound ablation element is adapted to emit a substantially circumferential pattern of ultrasound energy and to ablatively couple to a substantial portion of a circumferential region of tissue engaged by the inflatable balloon in the radially expanded position when the ultrasound ablation element is coupled to and actuated by an ultrasound ablation actuator.

3. A catheter according to claim 1, wherein the circumferential ablation element comprises an ultrasound transducer.

4. A catheter according to claim 3, wherein the ultrasound transducer is substantially tubular.

5. A catheter according to claim 4, wherein the ultrasound transducer is mounted in surrounding relation to the inner support member with a radial separation between at least a portion of the ultrasound transducer and an outer surface of the inner support member that forms a radial separation region with a gas-filled gap.

6. A catheter according to claim 5, wherein the radial separation region is sealed to substantially prevent fluid from entering from outside of the radial separation region into the gap.

7. A catheter according to claim 3, wherein the ultrasound transducer is adapted to emit a continuous circumferential pattern of ultrasound energy.

8. A catheter according to claim 3, wherein the ultrasound transducer is adapted to emit an acoustic signal at a frequency of between about 5 MHz to about 20 MHz.

9. A catheter according to claim 3, wherein the ultrasound transducer is adapted to emit an acoustic signal at a power level of at least about 20 Watts per centimeter radiator.

10. A catheter according to claim 1, wherein the expanded outer diameter of the inflatable balloon is at least about 1.0 centimeters when in the expanded position.

11. A catheter according to claim 1, wherein the moveable tube has a proximal end that extends out the proximal end of the catheter body.

12. A catheter according to claim 1, wherein the moveable tube has a lumen extending therethrough, wherein the lumen is open at the distal end of the moveable tube.

13. A catheter according to claim 12, wherein the moveable tube has a proximal end that extends out the proximal end of the catheter body and has a luer hub mounted thereon.

14. A catheter according to claim 1, further comprising a distal tubing mounted on the distal end of the moveable tube and having a proximal end to which the distal end of the balloon is attached.

15. A catheter according to claim 14, further comprising one or more electrodes mounted on the distal tubing.

16. A catheter according to claim 15, further comprising a tip electrode mounted on the distal tubing, the tip electrode having proximal and distal ends and an open passage extending therethrough.

17. A catheter according to claim 16, wherein the moveable tube has a lumen extending therethrough and a distal end positioned within the open passage of the tip electrode, wherein the lumen of the moveable tube is open at the distal end of the moveable tube, whereby fluid can pass through the moveable tube and out the distal end of the tip electrode.

18. A catheter according to claim 14, further comprising an elastic tubing having a proximal end attached to the distal end of the inner support member and a distal end attached to the proximal end of the distal tubing proximal to the position at which the distal end of the balloon is attached to the distal tubing.

19. A catheter according to claim 18, wherein the elastic tubing comprises silicone.

20. A catheter according to claim 1, wherein the inner support member is longitudinally moveable relative to the catheter body and moveable tube, whereby longitudinal movement of the inner support member relative to the catheter body and moveable tube causes longitudinal movement of the circumferential ablation element relative to the catheter body and moveable tube.

21. A catheter according to claim 20, wherein the proximal end of the inner support member extends out the proximal end of the catheter body.

22. A catheter according to claim 1, wherein the catheter body comprises a proximal region having a single lumen and a distal region having a plurality of lumens.

23. A catheter according to claim 1, further comprising means for deflecting the distal end of the catheter body.

24. A catheter according to claim 23, wherein the deflecting means comprises:

a puller wire extending through a lumen of the catheter body, said puller wire being fixedly attached at its distal end at or near the location of deflection; and a control handle for moving the puller wire longitudinally relative to the catheter body to thereby cause deflection.

25. A method for treating atrial arrhythmia by ablating a substantial portion of a circumferential region of tissue in a tubular region of or near the heart of a patient, comprising:

introducing into a patient a catheter according to claim 1, wherein the circumferential ablation element comprises an ultrasound ablation element coupled to an acoustic energy driver;

contacting a substantial portion of the circumferential region of tissue with at least a portion of the inflatable balloon, such that the ultrasound ablation element is positioned to deliver a substantially circumferential pattern of ultrasound energy through the inflatable balloon to the substantial portion of the circumferential region of tissue; and actuating the acoustic energy driver to ablatively couple the ultrasound ablation element to the substantial portion of the circumferential region of tissue via the inflatable balloon.

26. A method according to claim 25, wherein contacting at least the substantial portion of the circumferential region of tissue comprises expanding the inflatable balloon to radially engage the substantial portion of the circumferential region of tissue.

27. A method according to claim 26, wherein expanding the inflatable balloon comprises introducing an ultrasonically transparent inflation fluid to an inner region of the inflatable balloon.

28. A method according to claim 27, wherein the ultrasonically transparent inflation fluid comprises a radiopaque dye.

29. A method according to claim 26, further comprising longitudinally moving moveable tube relative to the catheter body to move the distal end of the balloon distally relative to the proximal end of the balloon.

30. A method according to claim 29, wherein the moveable tube is moved longitudinally after the balloon is expanded.

31. A method according to claim 25, wherein the moveable tube has a lumen extending therethrough, wherein the lumen is open at the distal end of the moveable tube, and further wherein the catheter is introduced over a guidewire that extends through the lumen of the moveable tube.

32. A method according to claim 25, wherein the catheter further comprises a distal tubing mounted on the distal end of the moveable tube and having a proximal end to which the distal end of the balloon is attached, wherein one or more electrodes are mounted on the distal tubing.

33. A method according to claim 32, further comprising mapping electrical activity in the tubular region of or near the heart using the one or more electrodes.

34. A catheter according to claim 25, wherein the inner support member is longitudinally moveable relative to the catheter body and moveable tube, the method further comprising longitudinally moving the inner support member relative to the catheter body and moveable tube to affect longitudinal movement of the circumferential ablation element relative to the catheter body and moveable tube.

35. A method according to claim 25, further comprising ablatively coupling the ultrasound ablation element to the substantial portion of the circumferential region of tissue at a location where cardiac tissue extends along the pulmonary vein.

36. A method according to claim 25, further comprising ablatively coupling the ultrasound ablation element to the substantial portion of the circumferential region of tissue at a location where cardiac tissue extends along an ostium of the pulmonary vein.

37. A method according to claim 25, further comprising ablatively coupling the ultrasound ablation element to the substantial portion of the circumferential region of tissue at a location along the atrial wall and surrounding an ostium of the pulmonary vein.

38. A method according to claim 25, further comprising actuating the ultrasound ablation element to emit the substantially circumferential pattern of ultrasound energy at a frequency ranging from about 5 MHz to about 20 MHz.

39. A method according to claim 25, wherein the entire circumferential region of tissue is ablatively coupled to the ultrasound ablation element.

\* \* \* \* \*

UNITED STATES PATENT AND TRADEMARK OFFICE
CERTIFICATE OF CORRECTION

PATENT NO. : 6,780,183 B2
DATED : August 24, 2004
INVENTOR(S) : Jimenez, Jr. et al.

It is certified that error appears in the above-identified patent and that said Letters Patent is hereby corrected as shown below:

Column 18,
Line 12, delete "centimeters", insert -- centimeter --.

Column 19,
Line 32, after "longitudinally moving", insert -- the --.

Column 20,
Line 15, delete "affect", insert -- effect --.

Signed and Sealed this

Eighteenth Day of October, 2005

JON W. DUDAS
*Director of the United States Patent and Trademark Office*